US010709753B2

(12) United States Patent
Zhu et al.

(10) Patent No.: US 10,709,753 B2
(45) Date of Patent: Jul. 14, 2020

(54) METHOD OF INHIBITING ANGIOGENESIS (71) Applicant: DAIWA PHARMACEUTICAL CO., LTD., Tokyo (JP)

(72) Inventors: Xia Zhu, Tokyo (JP); Naoki Igari, Tokyo (JP)

(73) Assignee: DAIWA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/400,849

(22) Filed: May 1, 2019

(65) Prior Publication Data
US 2019/0255137 A1    Aug. 22, 2019

Related U.S. Application Data (62) Division of application No. 15/779,021, filed as application No. PCT/JP2015/083238 on Nov. 26, 2015, now abandoned.

(51) Int. Cl.
*A61K 31/715* (2006.01)
*A61K 36/899* (2006.01)
(Continued)

(52) U.S. Cl.
CPC .......... *A61K 36/899* (2013.01); *A61K 31/715* (2013.01); *A61K 36/07* (2013.01);
(Continued)

(58) Field of Classification Search
CPC .................................................... A61K 31/715
See application file for complete search history.

(56) References Cited

U.S. PATENT DOCUMENTS 5,560,914 A    10/1996  Ghoneum et al.
5,997,875 A    12/1999  Zhou et al.

FOREIGN PATENT DOCUMENTS

BR    PI9603030 A    4/1998
DE    69516681 T2    2/2001
(Continued)

OTHER PUBLICATIONS

Yama et al., "Antitumor Effect of Rice Bran-Derived Glucosylceramide and Its Influence on Angiogenesis", Japanese Journal of Head and Neck Cancer, vol. 38, 2012, 6 pages. (English Abstract Submitted).
(Continued)

*Primary Examiner* — Rosanne Kosson
(74) *Attorney, Agent, or Firm* — Womble Bond Dickinson (US) LLP (57) ABSTRACT An angiogenesis inhibitor effective in inhibiting angiogenesis which causes a disease is obtained by, for example, sterilely filtrating, disinfecting, and concentrating a product which is obtained as follows. That is, rice bran is extracted with hot water, the insoluble matter is filtrated, and the starch is decomposed by processing the filtrate with glucoamylase, thereby obtaining a water-soluble polysaccharide extract. Ammonium sulfate is added to a culture filtrate prepared by culturing *Lentinula edodes* of basidiomycetes, thereby obtaining an enzyme complex from the precipitate. This enzyme complex is added to the water-soluble polysaccharide extract, and the mixture is caused to react at a pH of 4.5 for 30 to 60 min and further react at a pH of 6.0 for 30 to 60 min, thereby biologically modifying the water-soluble polysaccharide extract and obtaining the product.

2 Claims, 8 Drawing Sheets (51) Int. Cl.
*A61P 17/06* (2006.01)
*A61P 19/02* (2006.01)
*A61P 27/00* (2006.01)
*A61K 36/07* (2006.01)
*A61P 9/10* (2006.01)
*A61K 36/88* (2006.01)
*A61P 43/00* (2006.01)
*A61P 9/00* (2006.01)

(52) U.S. Cl.
CPC .............. *A61K 36/88* (2013.01); *A61P 9/00* (2018.01); *A61P 9/10* (2018.01); *A61P 17/06* (2018.01); *A61P 19/02* (2018.01); *A61P 27/00* (2018.01); *A61P 43/00* (2018.01)

(56) References Cited

FOREIGN PATENT DOCUMENTS

| EP | 0753582 A1 | 1/1997 |
| ES | 2147270 T3 | 9/2000 |
| JP | 09-023895 A | 1/1997 |
| JP | 2010-195728 A | 9/2010 |
| KR | 10-2003-0030636 A | 4/2003 |
| PT | 753582 E | 8/2000 |

OTHER PUBLICATIONS

Office Action received for Japanese Patent Application No. 2017-552614, dated Feb. 26, 2019, 4 pages (2 pages of English Translation and 2 pages of Office Action).

Office Action received for Japanese Patent Application No. 2017-552614, dated Dec. 26, 2018, 6 pages (3 pages of English Translation and 3 pages of Office Action).

Menon et al., "Value added products from hemicellulose: Biotechnological perspective", Global Journal of Biochemistry, vol. 1, Issue 1, 2010, pp. 36-67.

International Search Report and Written Opinion received for PCT Patent Application No. PCT/JP2015/083238, dated Feb. 16, 2016, 12 pages (6 pages of English Translation and 6 pages of Original Document).

International Preliminary Report on Patentability received for PCT Patent Application No. PCT/JP2015/083238, dated Jun. 7, 2018, 10 pages (6 pages of English Translation and 4 pages of Original Document).

Ghoneum et al., "Modified Arabinoxylan from Rice Bran, MGN-3/Biobran, Sensitizes Metastatic Breast Cancer Cells to Paclitaxel In Vitro", Anticancer Research, vol. 34, No. 1, 2014, pp. 81-87.

Folkman, Judah, "Angiogenesis in cancer, vascular, rheumatoid and other disease", Nature Medicine, vol. 1, 1995, pp. 27-31.

Ferrara, Napoleone, "Role of vascular endothelial growth factor in the regulation of angiogenesis", Kidney International, vol. 56, 1999, pp. 794-814.

European Search Report and Search Opinion Received for EP Application No. 15909274.1, dated Jun. 17, 2019, 9 pages.

Database WPI Week 201062, Thomson Scientific, London, G, AN 2010-L46332, XP002791251, 2 pages.

Database WPI Week 200380, Thomson Scientific, London, G, AN 2003-861453, XP002791298, 1 page.

Search Report received for IN Patent Application No. 201817017361, dated Jul. 24, 2019, 4 pages.

FIG.2B
Length

FIG.2C
Joint

FIG.2D
Path

METHOD OF INHIBITING ANGIOGENESIS

TECHNICAL FIELD

The present invention relates to an angiogenesis inhibitor which inhibits angiogenesis.

BACKGROUND ART

Attempts have been made to cure diseases such as a cancer by inhibiting angiogenesis. Angiogenesis is a physiological phenomenon in which a new blood vessel branches from existing blood vessel, and plays an important role in, for example, organogenesis and the development of a corpus luteum in the early development of an animal, and wound healing. It is known that excess occurrence of this angiogenesis participates in many diseases such as a malignant tumor, psoriasis, rheumatism, atherosclerosis, and retinopathy (see non-patent literatures 1 and 2).

The process of angiogenesis includes growth, differentiation, migration, tube formation of a vascular endothelial cell, and the like. Angiogenesis is mainly controlled by several different growth factors, and their receptors. Of these growth factors, a vascular endothelial growth factor (VEGF) is presumably the most important control factor in blood vessel formation. VEGF is a dimer glycoprotein specific to endothelial cells. Overexpression of VEGF occurs in various tumors, and causes blood vessel formation of a tumor. Overexpression of VEGF occurs in other pathological conditions such as chronic rheumatoid arthritis and retinal neovascularization.

The bond of two tyrosine kinase receptors, i.e., VEGF receptor 1 (VEGFR1) and VEGF receptor 2 (VEGFR2) intervenes the angiogenesis promoting action of VEGF. Since the tyrosine kinase activity of VEGFR2 is higher than that of VEGFR1, VEGFR2 is probably a central signal transmission path of angiogenesis.

When VEGF bonds to VEGFR2, dimerization and autophosphorylation of the receptor occur. This causes phosphorylation and activation of several downstream signaling proteins including Akt, ERK1/2, and p38MAPK. These signaling proteins play important roles in the survival, growth, migration, and reorganization of cancer cells.

RELATED ART LITERATURE

Non-Patent Literature

Non-Patent Literature 1: J. Folkman, "Angiogenesis in cancer, vascular, rheumatoid and other disease", Nature Medicine, vol. 1, pp. 27-31, 1995.
Non-Patent Literature 2: N. Ferrara, "Role of vascular endothelial growth factor in the regulation of angiogenesis", Kidney International, vol. 56, pp. 794-814, 1999.

SUMMARY OF INVENTION

Problem to be Solved by the Invention

As described above, angiogenesis participates in the development and progression of various diseases such as a malignant tumor, so angiogenesis inhibitors have been developed and used for the purposes of treatment and prevention. However, it is known that angiogenesis inhibitors presently being developed have side effects such as hemoptysis, nosebleed, thrombosis, hypertension, proteinurea, and perforation. Since angiogenesis inhibitors are often used for chronic diseases such as a malignant tumor, rheumatism, and arteriosclerosis, angiogenesis inhibitors need be taken for long time periods, so demands have arisen for a safe angiogenesis inhibitor. However, the use of angiogenesis inhibitors is limited due to the side effects as described above.

The present invention has been made to eliminate the problem as described above, and has as its object to provide a medicine that is effective in inhibiting angiogenesis causing a disease.

Means of Solution to the Problem

An angiogenesis inhibitor according to the present invention contains, as an effective component, a product produced by a process including a first process of obtaining a water-soluble polysaccharide extract by decomposing, by using glucoamylase, starch extracted from rice bran, a second process of adding ammonium sulfate to a culture filtrate prepared by culturing *Lentinula edodes* of basidiomycetes, and obtaining an enzyme complex from a precipitate, and a third process of biologically modifying the water-soluble polysaccharide extract obtained in the first process by adding the enzyme complex obtained in the second process to the water-soluble polysaccharide extract obtained in the first process, and causing the mixture to react at a pH of 4.0 to 5.0 for 30 to 60 min and further react at a pH of 5.5 to 6.5 for 30 to 60 min, and is used to inhibit angiogenesis.

In the abovementioned angiogenesis inhibitor, the product is a polysaccharide complex.

Effect of the Invention

As explained above, the present invention achieves a significant effect, that is, to provide a medicine effective in inhibiting angiogenesis causing a disease.

DETAILED DESCRIPTION OF THE INVENTION

Best Mode for Carrying Out the Invention

An embodiment of the present invention will be explained below. The manufacture of an angiogenesis inhibitor of the embodiment of the present invention will be explained.

First, a water-soluble polysaccharide extract is obtained by decomposing, by using glucoamylase, starch which is extracted by rice bran. For example, 5 L of water are added to 1,000 g of rice bran, and hot water extraction is performed for 60 min by heating the mixture to 100° C. After that, the insoluble matter is filtered out. After starch is extracted from rice bran by hot water and the insoluble matter is filtered out as described above, a rice bran hemicellulose extract is obtained by hydrolyzing starch in the filtrate by glucoamylase. A material other than rice bran can also be used as long as the material is hemicellulose. In particular, hemicellulose of grasses is excellent as a material.

Then, an enzyme complex is formed by culturing *Lentinula edodes* of basidiomycetes. Note that Lentinula edodes is usually also called *Lentinus edodes*. Table 1 below shows the medium composition.

TABLE 1

| Medium Composition of Lentinula edodes | |
| --- | --- |
| Distilled water | 1 L |
| Sucrose | 5 g |
| $NH_4NO_3$ | 10 g |
| $KH_2PO_4$ | 5 g |
| $MgSO_4$ | 2.5 g |
| $FeSO_4$ | Small amount |
| Culture conditions | pH 4.5, 20° C., 14 days |

After culture is performed in the above-described medium, ammonium sulfate is added to the culture filtrate so as to obtain 50% saturation, and the produced precipitate is separated, thereby obtaining an enzyme complex (Enzyme-LE) of *Lentinula edodes*.

After Enzyme-LE is obtained as described above, 3 g of the obtained Enzyme-LE are added to 4.5 L of the above-described rice bran hemicellulose (water-soluble saccharide). Initially, the pH is adjusted to 4.5, and the mixture is caused to react at 40° C. for 30 min. Then, the pH is adjusted to 6.0, and the mixture is caused to react for 30 min, thereby forming rice bran hemicellulose (RBX-LE: a product) modified by an extracellular enzyme of *Lentinula edodes*. Note that the first reaction need only be caused at a pH of 4.0 to 5.0 for 30 to 60 min. Note also that the second reaction need only be caused at a pH of 5.5 to 6.5 for 30 to 60 min. The formed product is an effective component of the angiogenesis inhibitor of this embodiment. It is found by analysis that the main component of the product as this effective component is xylan mainly containing a β-1,4 xylopyranose chain.

As explained above, the angiogenesis inhibitor of the present invention contains, as an effective component, a product which is produced as follows. That is, starch obtained from rice bran is decomposed by glucoamylase, thereby obtaining a water-soluble polysaccharide extract. Ammonium sulfate is added to a culture filtrate obtained by culturing *Lentinula edodes* of basidiomycetes, thereby obtaining an enzyme complex from the precipitate. The obtained enzyme complex is added to the water-soluble polysaccharide extract, and the mixture is caused to react at a pH of 4.0 to 5.0 for 30 to 60 min and further react at a pH of 5.5 to 6.5 for 30 to 60 min, thereby biologically modifying the water-soluble polysaccharide extract and obtaining the product. This angiogenesis inhibitor is used to inhibit angiogenesis. The product is a polysaccharide complex.

For example, the product formed as described above can be used as a liquid angiogenesis inhibitor through sterile filtration, disinfection, and direct concentration. It is also possible to powder the product by freeze drying or spray drying, and use the powder as a tableted or granulated angiogenesis inhibitor.

The physicochemical properties of RBX-LE are as shown in Table 2 below.

TABLE 2

| | RBX-LE |
| --- | --- |
| Average molecular weight | 600,000 daltons |
| Constituent sugars | Arabinose 26% |
| | Xylose 48% |
| | Galactose 7% |
| | Glucose 6% |
| | Mannose 9% |
| | Others 4% |

Next, the effects of the angiogenesis inhibitor of this embodiment described above will be explained by using examples.

Example 1

First, Example 1 will be explained. In Example 1, human umbilical vein endothelial cells (HUVECs) and human dermal fibroblasts (HDF) were used as targets of an angiogenesis inhibition model.

<Contents of Experiments>

HUVECs and HDF were allowed to coexist and cultured by adding 10 ng/mL of VEGF, adding no VEGF, adding the angiogenesis inhibitor of the embodiment, and adding no angiogenesis inhibitor. The addition amounts of the angiogenesis inhibitor were 0.3 mg/mL, 1 mg/mL, and 3 mg/mL.

Figure 1A:
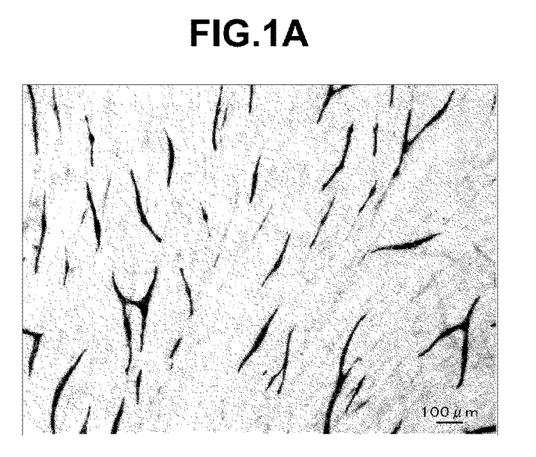
FIG. 1A is a photograph showing the result of culture performed by making HUVECs and HDF coexist and without adding anything.
Figure 1B:
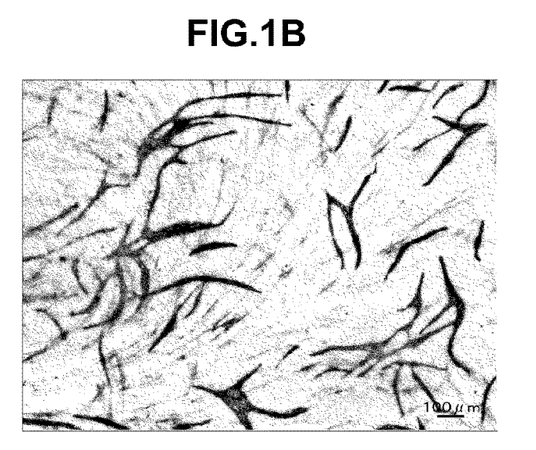
FIG. 1B is a photograph showing the result of culture performed by making HUVECs and HDF coexist and adding VEGF.
Figure 1C:
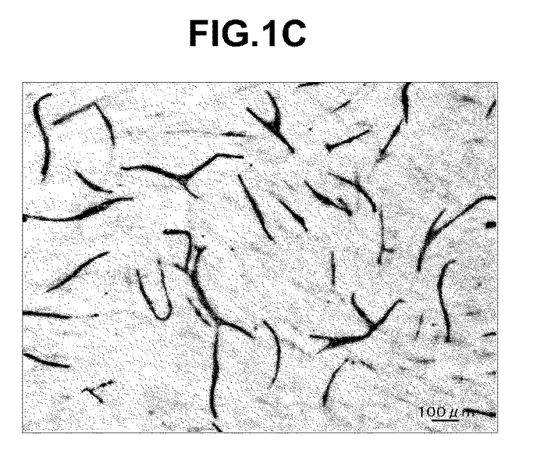
FIG. 1C is a photograph showing the result of culture performed by making HUVECs and HDF coexist and adding 0.3 mg/mL of an angiogenesis inhibitor in addition to VEGF.
Figure 1D:
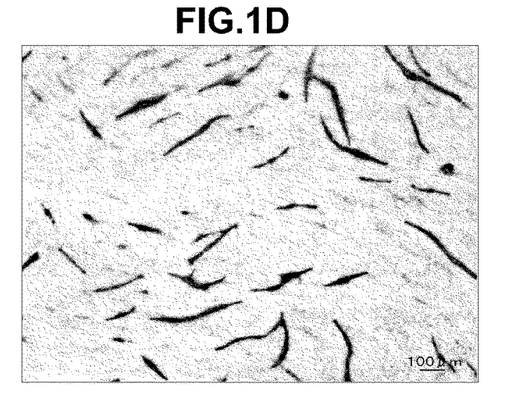
FIG. 1D is a photograph showing the result of culture performed by making HUVECs and HDF coexist and adding 1 mg/mL of the angiogenesis inhibitor in addition to VEGF.
Figure 1E:
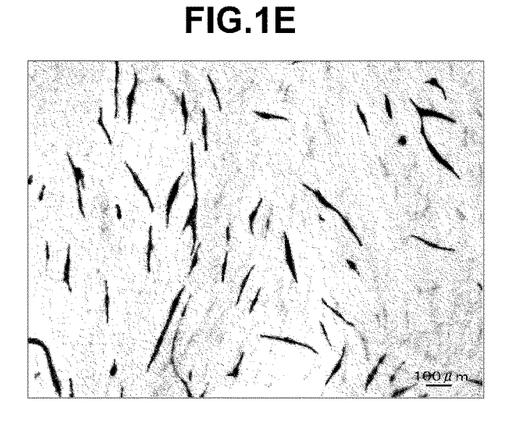
FIG. 1E is a photograph showing the result of culture performed by making HUVECs and HDF coexist and adding 3 mg/mL of an angiogenesis inhibitor in addition to VEGF.

After the elapse of 10 days, each cultured state was observed with an optical microscope. FIGS. 1A, 1B, 1C, 1D, and 1E show photographs obtained by the observation. FIG. 1A is a photograph showing the result of culture performed by adding nothing. FIG. 1B is a photograph showing the result of culture performed by adding VEGF. FIG. 1C is a photograph showing the result of culture performed by adding 0.3 mg/mL of the angiogenesis inhibitor in addition to VEGF. FIG. 1D is a photograph showing the result of culture performed by adding 1 mg/mL of the angiogenesis inhibitor in addition to VEGF. FIG. 1E is a photograph showing the result of culture performed by adding 3 mg/mL of the angiogenesis inhibitor in addition to VEGF.

Figure 2A:
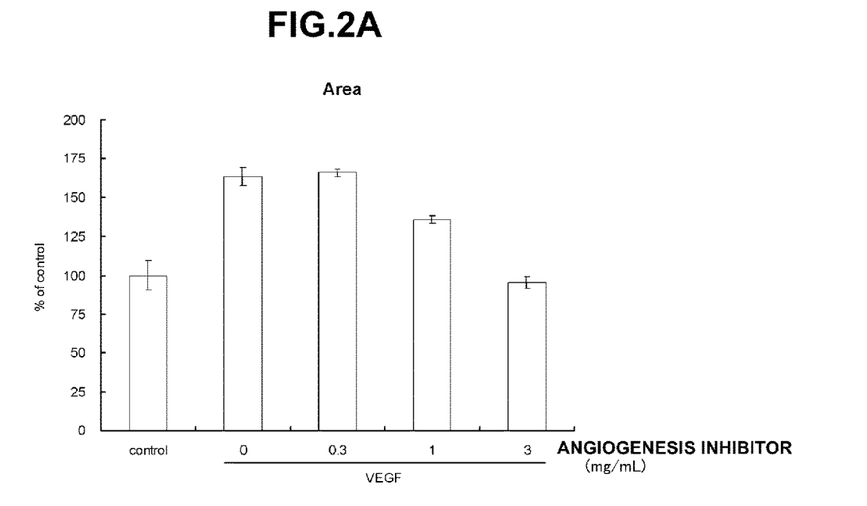
FIG. 2A is a figure showing the results of quantitative determination, which is performed by image data processing in optical microscopic observation, of the areas of tubes obtained 10 days after culture performed by making HUVECs and HDF coexist under different conditions.
Figure 2B:
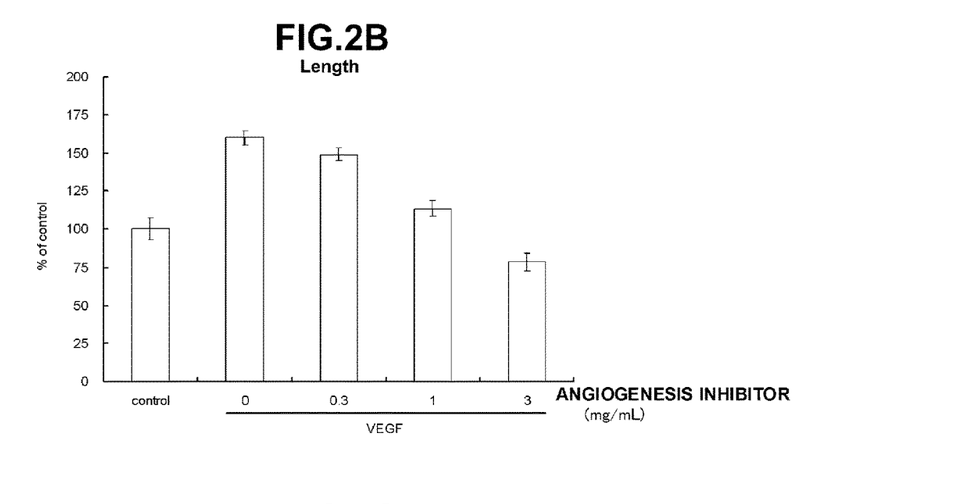
FIG. 2B is a figure showing the results of quantitative determination, which is performed by image data processing in optical microscopic observation, of the lengths of tubes obtained 10 days after culture performed by making HUVECs and HDF coexist under different conditions.
Figure 2C:
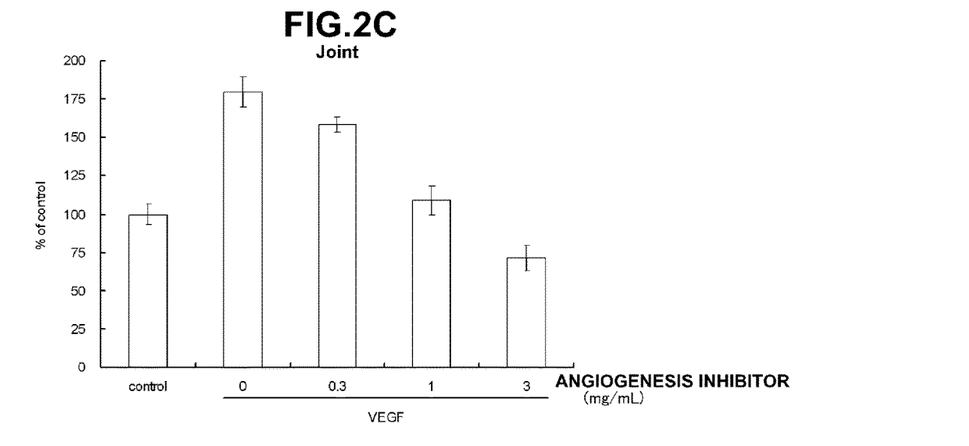
FIG. 2C is a figure showing the results of quantitative determination, which is performed by image data processing in optical microscopic observation, of the number of joints of tubes obtained 10 days after culture performed by making HUVECs and HDF coexist under different conditions.
Figure 2D:
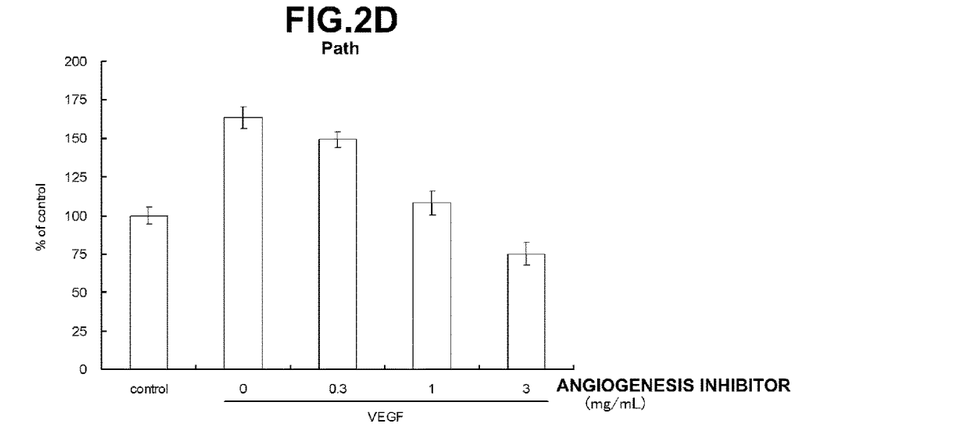
FIG. 2D is a figure showing the results of quantitative determination, which is performed by image data processing in optical microscopic observation, of the number of paths of tubes obtained 10 days after culture performed by making HUVECs and HDF coexist under different conditions.

Also, the results of tube formation (the area, the length, the number of joints, and the number of paths) after 10 days culture were quantitatively determined by imaging (image) data processing in optical microscopic observation. This quantitative determination was performed by processing the image data shown in FIGS. 1A, 1B, 1C, 1D, and 1E. The quantitative determination was performed by analysis using angiogenesis quantitative determination software Ver. 2 (available from KURABO). FIG. 2A is a figure showing the quantitative determination results of the area. FIG. 2B is a figure showing the quantitative determination results of the length. FIG. 2C is a figure showing the quantitative determination results of the number of joints. FIG. 2D is a figure showing the quantitative determination results of the number of paths. In each figure, "control" indicates the result of culture performed by adding nothing.

<Results of Experiments>

As shown in FIGS. 2A, 2B, 2C, and 2D, the results of quantitative determination reveal that when the angiogenesis inhibitor of the embodiment was added, tube formation was inhibited in a concentration-dependent manner in any of the area, the length, the number of joints, and the number of paths of the blood vessel. When the angiogenesis inhibitor of the embodiment was added, a significant difference from the case in which only VEGF was added was found when the addition amount was 3 mg/mL for the area, and when the addition amounts were 1 and 3 mg/mL for the length, the number of joints, and the number of paths.

Example 2

Next, Example 2 will be explained. In Example 2, HUVECs were used as targets of an angiogenesis inhibition model.

<Contents of Experiments>

After HUVECs were cultured for 24 hrs, HUVECs were further cultured for 72 hrs by adding 10 ng/mL of VEGF, adding no VEGF, adding the angiogenesis inhibitor of the embodiment, and adding no angiogenesis inhibitor. The addition amounts of the angiogenesis inhibitor were 0.3 mg/mL, 1 mg/mL, and 3 mg/mL. In addition, 10 μL of MTT were added to each cultured sample, and a formazan product was measured with a microplate reader after the elapse of 4 hrs.

<Results of Experiments>

Figure 3:
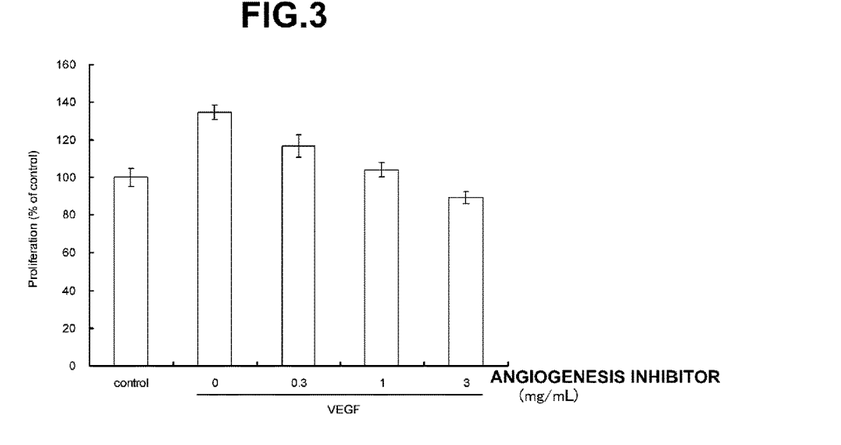
FIG. 3 is a figure showing the results of measurement performed on a formazan product by using a microplate reader, in the results of culture performed under the different conditions in Example 2.

As shown in FIG. 3, the results of measurement indicate that the angiogenesis inhibitor of the embodiment inhibited the growth of HUVECs in a concentration-dependent manner. The larger the addition amount of the angiogenesis inhibitor, the more the growth of HUVECs was inhibited. When the addition amounts of the angiogenesis inhibitor were 1 mg/mL and 3 mg/mL, significant differences were found compared to the case (control) in which VEGF was added but no angiogenesis inhibitor was added.

Example 3

Example 3 will be explained below. In Example 3, HUVECs were used as targets, and cell migration states were measured, as an angiogenesis inhibition model.

<Contents of Experiments>

To measure the migration of cells, culture was performed for 24 hrs so as to grow a single layer of HUVECs in a collagen-coated vessel. By this culture, HUVECs grew in the form of a sheet on the bottom of the vessel. This layer of HUVECs having grown in the form of a sheet was aseptically scratched, thereby forming a portion having no cells. Cells floated by scratch were removed, and culture was performed for 21 hrs by adding 10 ng/mL of VEGF, adding no VEGF, adding the angiogenesis inhibitor of the embodiment, and adding no angiogenesis inhibitor. The addition amounts of the angiogenesis inhibitor were 0.3 mg/mL, 1 mg/mL, and 3 mg/mL.

Figure 4A:
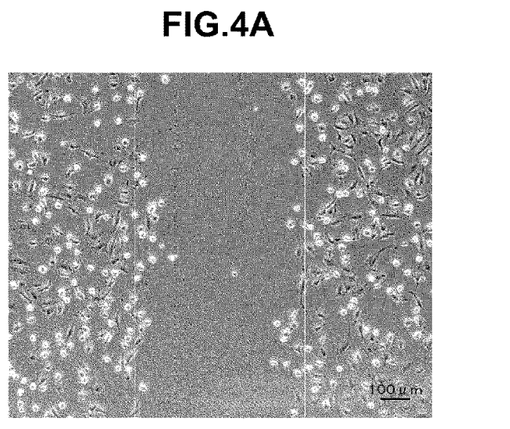
FIG. 4A is a photograph showing the result of culture performed by without adding anything in Example 3.
Figure 4B:
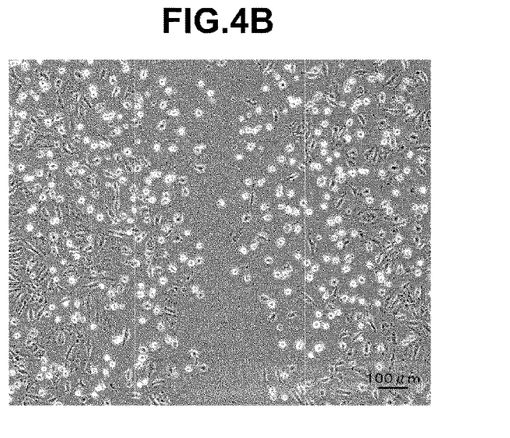
FIG. 4B is a photograph showing the result of culture performed by adding VEGF in Example 3.
Figure 4C:
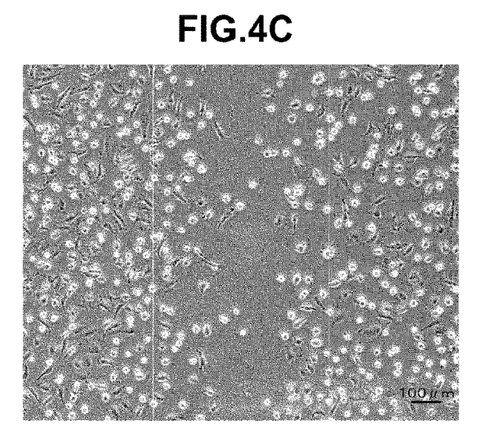
FIG. 4C is a photograph showing the result of culture performed by adding 0.3 mg/mL of an angiogenesis inhibitor in addition to VEGF in Example 3.
Figure 4D:
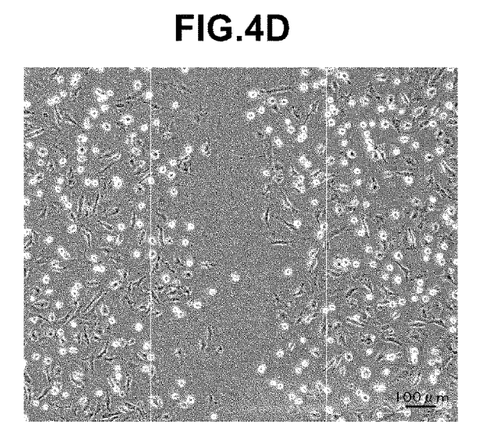
FIG. 4D is a photograph showing the result of culture performed by adding 1 mg/mL of the angiogenesis inhibitor in addition to VEGF in Example 3.
Figure 4E:
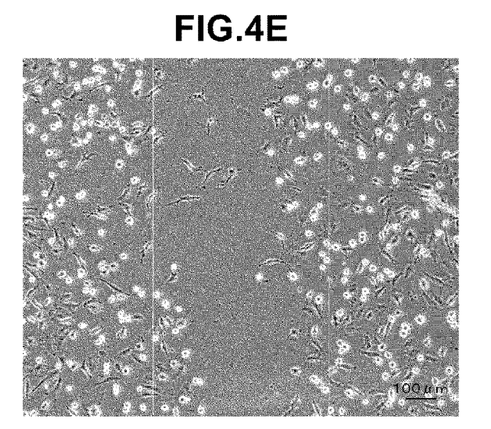
FIG. 4E is a photograph showing the result of culture performed by adding 3 mg/mL of the angiogenesis inhibitor in addition to VEGF in Example 3.

The number of cells in the scratched portion of each cultured sample was observed with an optical microscope. FIGS. 4A, 4B, 4C, 4D, and 4E show optical microscopic photographs of the samples. FIG. 4A is a photograph showing the result of culture performed by adding nothing. FIG. 4B is a photograph showing the result of culture performed by adding VEGF. FIG. 4C is a photograph showing the result of culture performed by adding 0.3 mg/mL of the angiogenesis inhibitor in addition to VEGF. FIG. 4D is a photograph showing the result of culture performed by adding 1 mg/mL of the angiogenesis inhibitor in addition to VEGF. FIG. 4E is a photograph showing the result of culture performed by adding 3 mg/mL of the angiogenesis inhibitor in addition to VEGF.

<Results of Experiments>

Figure 5:
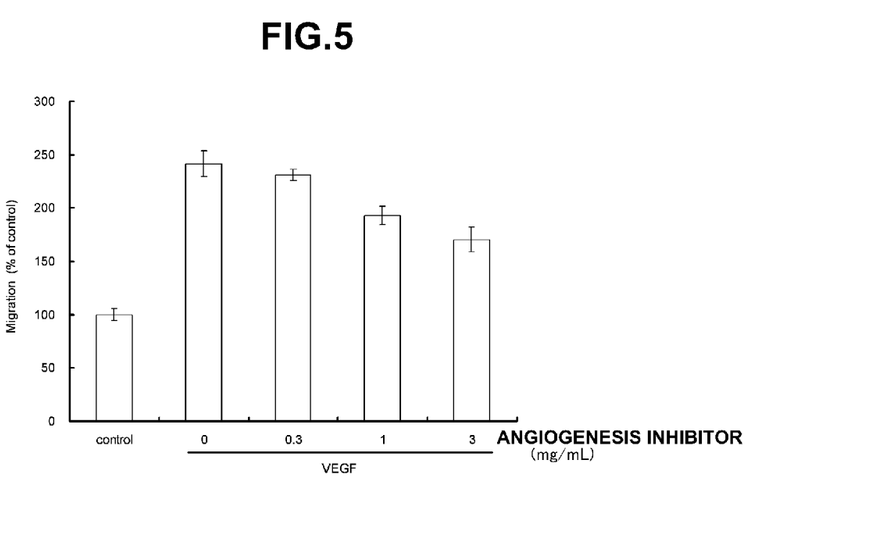
FIG. 5 is a figure showing measurements performed by optical microscopic observation on cell migration states under different conditions of Example 3.

As shown in FIG. 5, the results of measurement of the migration states demonstrate that the angiogenesis inhibitor inhibited the migration of HUVECs in a concentration-dependent manner. The larger the addition amount of the angiogenesis inhibitor, the more the migration of HUVECs was inhibited. When the addition amounts of the angiogenesis inhibitor were 1 mg/mL and 3 mg/mL, significant differences were found compared to the case (control) in which VEGF was added and no angiogenesis inhibitor was added.

Example 4

Example 4 will be explained below. In Example 4, HUVECs were used as targets of an angiogenesis inhibition model.

<Contents of Experiments>

Figure 6:
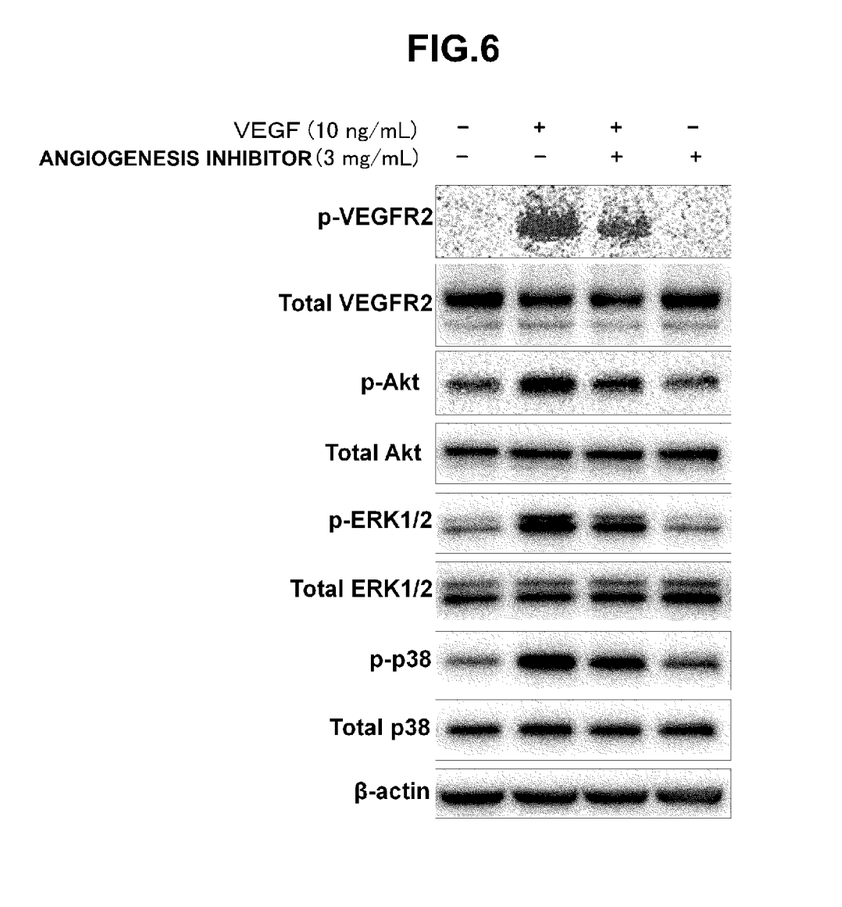
FIG. 6 is a photograph showing the results of western blot analysis performed on cell extracts under different conditions of HUVECs in Example 4.
Figure 7A:
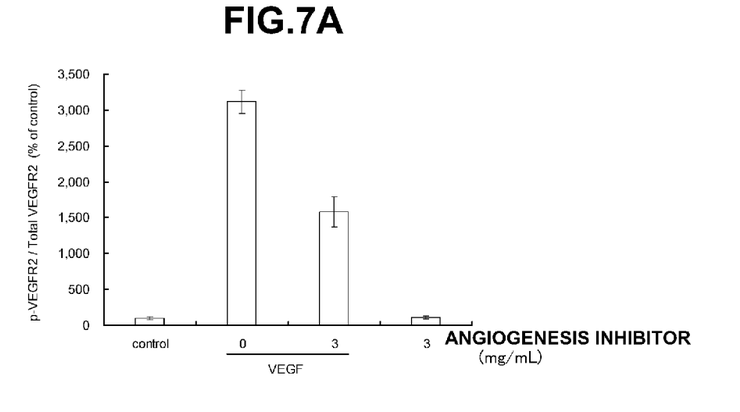
FIG. 7A is a figure showing phosphorylation of VEGFR2 under the different conditions of Example 4.
Figure 7B:
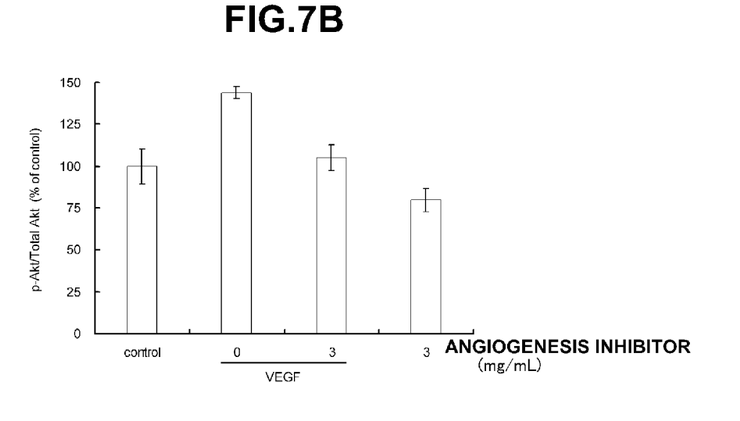
FIG. 7B is a figure showing phosphorylation of Akt under the different conditions of Example 4.
Figure 7C:
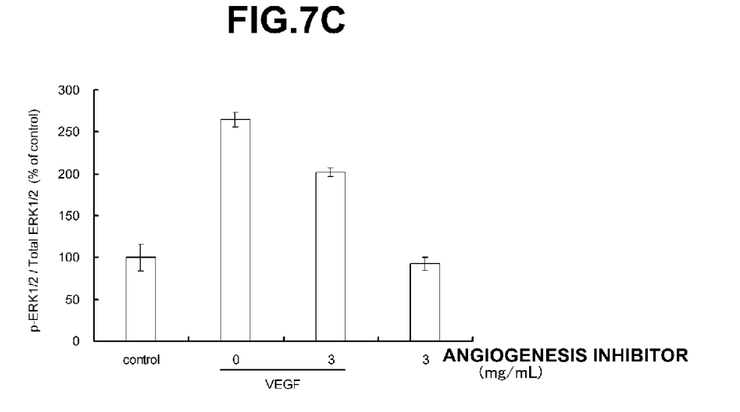
FIG. 7C is a figure showing phosphorylation of ERK1/2 under different conditions of Example 4.
Figure 7D:
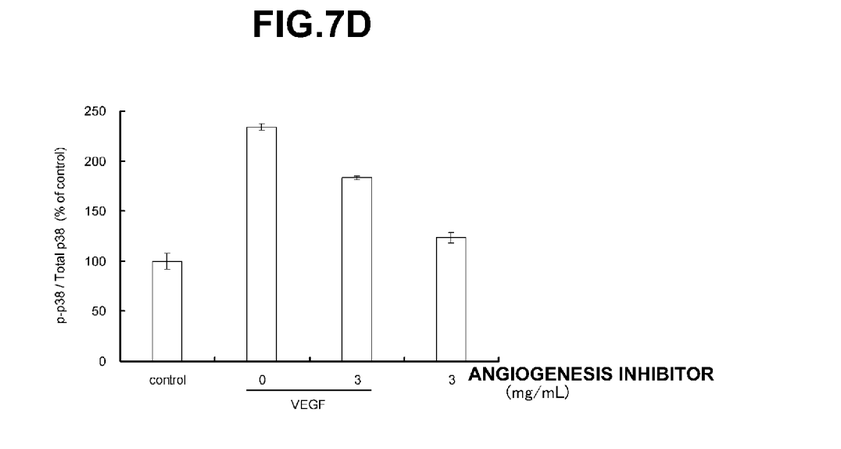
FIG. 7D is a figure showing phosphorylation of p38 under the different conditions of Example 4.

HUVECs were analyzed by western blotting in order to check whether the effect of the angiogenesis inhibitor participates in the inhibition of VEGFR2 and its downstream signaling proteins. HUVECs were pre-cultured for 30 min by adding the angiogenesis inhibitor (3 mg/mL) and adding no angiogenesis inhibitor. VEGF (10 ng/mL) was added to each obtained material, and the material was cultured for 15 min. HUVECs were dissolved and centrifugally separated, and the supernatant was collected, thereby extracting proteins. The extracted proteins were analyzed by western blotting. An image was captured by an image capturing apparatus "Ez-Capture MG AE-9300 (available from ATTO)" and analyzed by analysis software "CS Analyzer 3.0 (available from ATTO)". FIG. 6 shows the results of image capturing. FIGS. 7A, 7B, 7C, and 7D show the results of analysis.

<Results of Experiments>

The results of HUVECs analysis reveal that the addition of VEGF increased phosphorylation of VEGFR2 as a vascular endothelial growth factor receptor, Akt as serine/threonine kinase, ERK1/2 and p38 as mitogen-activated protein kinases. The results of analysis also indicate that the pretreatment of the angiogenesis inhibitor inhibits phosphorylation of the above-described signaling proteins which participate in angiogenesis. Note that as indicated by "β-actin" in FIG. 6, the total protein amounts in the applied HUVECs extract samples were equal.

As explained above, the angiogenesis inhibitor of the present invention is effective in inhibiting angiogenesis which causes a disease.

The invention claimed is:

1. A method of inhibiting angiogenesis by human vascular endothelial cells (HUVECs) in a subject in need thereof, by administering to a site in the subject comprising the inhibitor, wherein the angiogenesis inhibitor is produced by a process comprising:
   I. a first step of obtaining a water-soluble polysaccharide extract, by
      a) obtaining rice bran;
      b) extracting the starch from the rice bran;
      c) contacting the starch with a glucoamylase to digest the starch, thereby making water-soluble polysaccharides; and
      d) separating the water-soluble polysaccharides from the mixture in step (c), thereby making the water-soluble polysaccharide extract;
   II. a second step of:
      e) adding ammonium sulfate to a culture filtrate prepared by culturing *Lentinus edodes* of basidiomycetes, thereby precipitating an enzyme complex from the culture filtrate, and
      f) harvesting the enzyme complex from the precipitate; and
   III. a third step of biologically modifying the water-soluble polysaccharide extract obtained in step (I) by adding the enzyme complex obtained in step (II) to the water-soluble polysaccharide extract obtained in step (I), and causing the mixture to react at a pH of 4.0 to 5.0 for 30 to 60 min and further to react at a pH of 5.5 to 6.5 for 30 to 60 min.

2. The method of inhibiting angiogenesis according to claim 1, wherein the water-soluble polysaccharide extract obtained in step (III) comprises a mixture of polysaccharides.

* * * * *